United States Patent
Papageorgiou et al.

(10) Patent No.: US 8,995,734 B2
(45) Date of Patent: Mar. 31, 2015

(54) IMAGE PROCESSING METHOD AND SYSTEM

(75) Inventors: Pavlos Papageorgiou, Edinburgh (GB); Ian Poole, Edinburgh (GB)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 446 days.

(21) Appl. No.: 13/347,396

(22) Filed: Jan. 10, 2012

(65) Prior Publication Data

US 2013/0177224 A1   Jul. 11, 2013

(51) Int. Cl.

| G06K 9/00 | (2006.01) |
|---|---|
| G06F 19/00 | (2011.01) |
| G06K 9/62 | (2006.01) |
| G06T 7/00 | (2006.01) |
| A61B 5/00 | (2006.01) |
| A61B 5/055 | (2006.01) |
| A61B 6/03 | (2006.01) |
| A61B 6/00 | (2006.01) |

(52) U.S. Cl.
CPC ............ *A61B 5/0035* (2013.01); *A61B 5/0013* (2013.01); *A61B 5/055* (2013.01); *A61B 5/7246* (2013.01); *A61B 6/032* (2013.01); *A61B 6/037* (2013.01); *A61B 6/5235* (2013.01); *A61B 6/5247* (2013.01); *G06F 19/321* (2013.01); *G06F 19/324* (2013.01); *G06K 9/6206* (2013.01); *G06T 7/0024* (2013.01); *G06T 2207/10081* (2013.01); *G06T 2207/10088* (2013.01); *G06T 2207/10104* (2013.01)
USPC .......................... 382/131; 382/276; 382/278

(58) Field of Classification Search
None
See application file for complete search history.

(56) References Cited

U.S. PATENT DOCUMENTS

| 7,298,869 | B1 * | 11/2007 | Abernathy ................. 382/108 |
|---|---|---|---|
| 7,386,187 | B2 * | 6/2008 | Solomon et al. ............ 382/276 |
| 2005/0271301 | A1 * | 12/2005 | Solomon et al. ............ 382/294 |
| 2009/0136102 | A1 * | 5/2009 | Kimpe et al. ............... 382/128 |
| 2012/0027278 | A1 * | 2/2012 | Chaney et al. .............. 382/131 |
| 2013/0194261 | A1 * | 8/2013 | Cummins et al. ........... 345/420 |

* cited by examiner

*Primary Examiner* — Shefali Goradia
(74) *Attorney, Agent, or Firm* — Oblon, McClelland, Maier & Neustadt, L.L.P.

(57) ABSTRACT

A method of processing image data including performing a first mapping, of a first image dataset to a first reference, performing a second mapping, of a second image dataset to a second reference, and using the first mapping and the second mapping to correlate at least one position in the first image dataset to at least one position in the second image dataset.

21 Claims, 6 Drawing Sheets

IMAGE PROCESSING METHOD AND SYSTEM

FIELD

Embodiments described herein relate generally to an image processing method and system, and in particular to a method and system for processing and correlating medical image data obtained using different medical imaging apparatus or at different times.

BACKGROUND

In the processing of medical imaging data it is often useful to show the same anatomical location in different scans, for example CT, MR, or PET scans, of the same patient.

For example, processing a CT chest exam usually requires reference to prior chest CT exams performed on the same patient, which may have been acquired using various different CT scanners. In another example, many conditions are diagnosed using both a CT and an MR exam of the same part of the body. In that case, more accurate or informative results can be obtained by displaying or otherwise processing the results of both the CT and the MR scan in combination. That is especially true of processing for display, where the goal can be to create images that are correlated spatially to show the same anatomy as it appears in each of the CT and MR datasets.

It may also be desired to correlate measurements of particular features or types of features, for example lung nodules, obtained at different times using the same or different imaging modalities.

The time difference between when one scan and another scan on the same patient is performed may be short, for example hours or days, or long, for example years. The need to process together data obtained from different scans, or to use information derived from one scan in analysis of another scan, can present significant technical difficulties particularly when the scans are widely separated in time, or are obtained at different locations.

In one specific example, a patient may have a chest CT scan in Shanghai in 2004, which is reported as being normal. The same patient may have a chest CT scan in Tokyo in 2005 and two nodules may be found. It may be desired to check the location of the nodules in the CT dataset obtained in 2004 to verify disease progression. However, technical, legal or other reasons may prevent sharing of three-dimensional datasets between hospitals, particularly hospitals in different countries and particularly given the large size of the three dimensional datasets.

In another example, a patient suffering a seizure may have a brain MR scan in 2002 and subsequently be treated for cerebral oedema. The same patient may have an emergency CT scan in 2009 after having suffered a stroke. It would be desirable to indicate in the emergency CT scan data the area in which the patient previously suffered the cerebral oedema. However, the three-dimensional MR dataset obtained in 2002 may have been deleted due to limited storage space. Only two-dimensional key image data may have been saved in accordance with what is usual practice in many hospitals. Thus, it may not be possible to accurately indicate the desired area.

In a further example, a patient may have an abdominal CT scan in a Sao Paulo hospital. A liver lesion may be detected which is considered benign or to be monitored. A mobile CT truck then visits a remote Brazilian town three months later and a CT scan is performed on the same patient. It would be desirable for the CT operator in the truck to show the CT data obtained in the hospital side-by-side with the CT data obtained by the CT scanner in the truck. However, there may be limited wireless bandwidth available to transmit data between the truck and the hospital, making it difficult or impossible in practice to share data between the CT truck and the hospital.

The above examples relate to situations in which data is to be shared between widely separated locations, or data is obtained at widely separated points in time. However, there can also be problems with sharing data even between systems located in the same hospital, particularly if a distributed server architecture is used.

In many known systems, a central server is connected to many different imaging apparatuses, for example many different CT or MR scanners, via a network. Each imaging apparatus sends the results of measurements that it performs to the central server, where they are logged and stored, usually in a picture archiving and communication (PACS) system. The results are usually in the form of image datasets comprising one or a sequence of images. Images may be viewed and processed by an operator at the imaging apparatus.

If correlation of images or other results obtained from different imaging apparatus or at different times is required, then the processing of the images or other results to obtain such correlation is usually performed at the central server. The position of anatomical features will almost always be different in image datasets obtained at different times or using different apparatus. In known systems, if two image datasets stored at the server are to be correlated, the server usually performs a rigid or non-rigid registration process in accordance with well-known techniques. For example, it is common diagnostic practice to identify one image dataset as a reference, and to register other image datasets to that reference, or to register different image datasets in a pairwise fashion.

It is also known to register image datasets from many different patients to an atlas to enable a comparison with a common reference, for example for the purposes of medical research.

More recently, it has been suggested that a distributed server architecture can be used to process data from a plurality of imaging apparatus, in which a separate server is associated with each imaging apparatus. For example one server is attached to a CT scanner, another server is attached to an MR scanner, a further server is attached to a further CT scanner. The individual servers are connected to each other and to at least one client via a network. Although the servers are interconnected, each server is configured to store and process the medical image data generated by its associated imaging apparatus. For example, the server attached to a CT scanner processes and stores the CT data, the server attached to a second CT scanner processes and stores the data from that second CT scanner and the server attached to an MR scanner processes and stores the MR data.

In such a distributed server system, a processing application running on a first server associated with a first CT scanner can access the data from that CT scanner directly but can only access data from a second CT scanner, or from an MR scanner, by requesting a time-consuming data transfer via the network. In order to correlate the location of features across N datasets a naïve implementation may require up to $O(N^2)$ comparisons of datasets, where each comparison generates a registration between the two datasets. A more advanced implementation, where one data set is designated as reference, may still require up to O(N) comparisons where each of the other datasets is registered with the reference. An implementation of a registration and correlation process of N datasets using the distributed system described in the previous paragraph may result in up to $O(N^2)$ transmissions of CT or MR datasets through the network, as each application attempts to access the data that it needs for a direct comparison. Even if it were practical to designate one dataset as reference, it would still be necessary to transmit up to $O(N)$ datasets to one server to perform the registrations. The transmission and processing of such large quantities of data is both time-consuming and inefficient.

BRIEF DESCRIPTION OF THE DRAWINGS

Embodiments are now described, by way of non-limiting example, and are illustrated in the following figures, in which.

DETAILED DESCRIPTION

Figure 1:
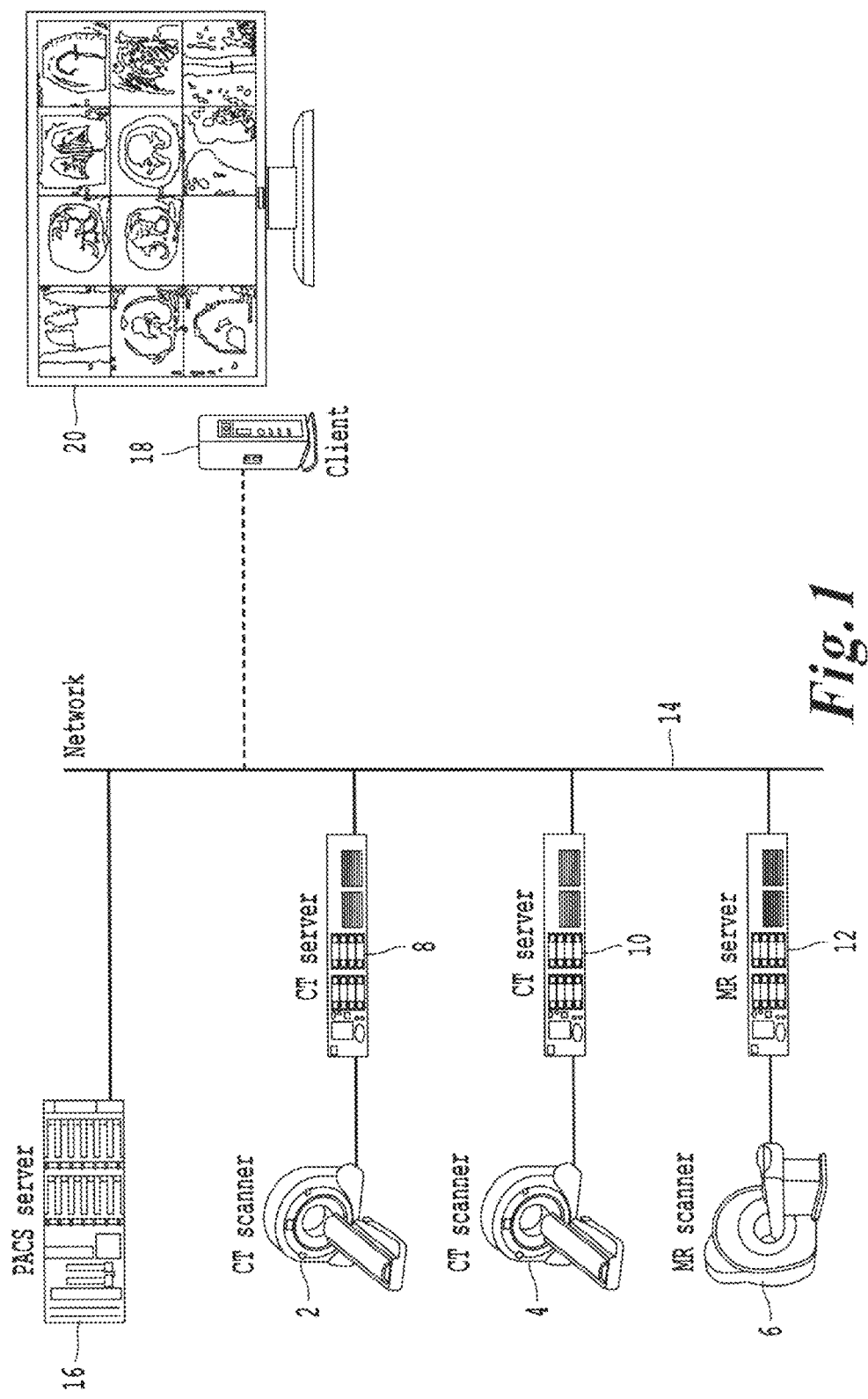
FIG. 1 is a schematic illustration of an image data processing system according to an embodiment.

According to one embodiment, there is provided a method of processing image data comprising performing a first mapping, of a first image dataset to a first reference, performing a second mapping, of a second image dataset to a second reference, and using the first mapping and the second mapping to correlate at least one position in the first image dataset to at least one position in the second image dataset. A system configured to put into effect the method described in the previous paragraph is illustrated in FIG. 1.

The system comprises two CT scanners 2, 4 and an MR scanner 6. Each scanner 2, 4, 6 has an associated server. Thus, CT scanner 2 is connected to CT server 8, CT scanner 4 is connected to CT server 10, and MR scanner 6 is connected to MR server 12.

The servers 8, 10, 12 are connected via a network 14 to a PACS server 16, and also to client devices that are operable to present imaging results and the results of processing of images to users. A single client device 18, in the form of a PC, and associated display 20 is shown in FIG. 1.

It will be understood that although two CT scanners and a single MR scanner are shown in FIG. 1, the system can include any number and type of different scanners and associated servers.

Figure 2:
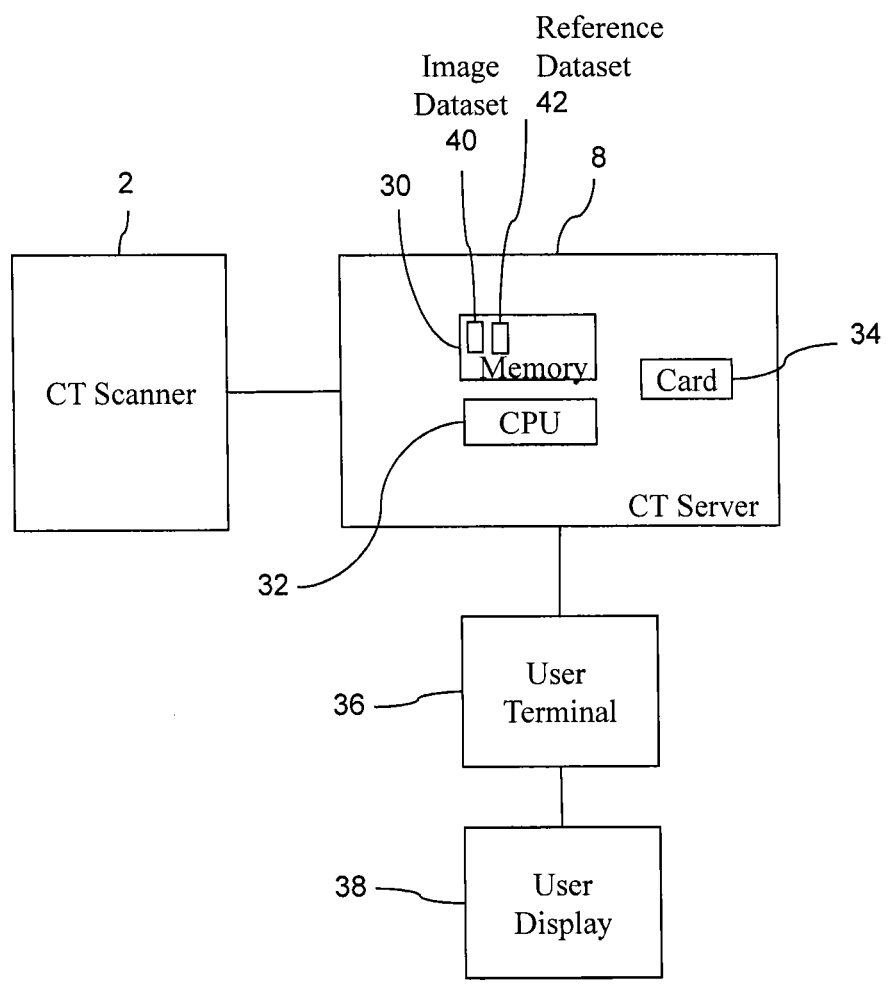
FIG. 2 is a schematic diagram showing a server associated with an imaging apparatus of the embodiment of FIG. 1.

A server 8 is shown in more detail in FIG. 2. The server 8 includes a memory 30, in this case a hard disk drive or array of hard disk drives, a processing resource in the form of a CPU 32, and a network card 34 for communicating with the network 14. The server 8 can also be connected to a user terminal 36 and associated user display 38 that can be used by an operator to instruct the performance of various image processing procedures and to display image data.

The results of the imaging measurements performed by each scanner are stored, in the form of image datasets 40 in memory 30 of CT server 8. The memory also stores a reference dataset 42 in the form of an atlas dataset. The use of the reference dataset in the processing of image datasets from different servers is described in more detail below.

The CPU 32 is configured to perform any desired image processing procedure, including for example image analysis functions such as measurement or identification of structures, or rendering functions such as presenting cross sections, projections, surface renderings, and other synthetic images generated from the acquired data.

In operation, the scanners 2, 4, 6 perform imaging measurements on patients or other subjects, and store the image data in their associated servers 8, 10, 12. The servers 8, 10, 12 perform image processing procedures on the stored datasets obtained from their associated scanner 2, 4, 6. It is a feature of the embodiment of FIG. 1 that upon obtaining each image dataset, each server 8, 10, 12 automatically registers it to the atlas dataset stored in the server and stores registration data representative of the registration together with the dataset, as described in more detail below. In other embodiments, the registration process is performed only when requested by an operator, by another process, or in response to a request from another device.

The plurality of servers 8, 10, 12 is able to present the results of processing the image data to users, such as radiologists or other medical professionals, using thin client technology at the client device 18. Connections are established from the one or more servers to a client application running on the client device 18 using a TCP/IP or similar network. The client application is able to display the imaging results of multiple servers 8, 10, 12 simultaneously. It also provides a user interface, coupled to a sub-system for transmitting control information originated by the user back to the appropriate server.

As discussed, it can be necessary or desirable for many image processing procedures to process or display in combination image datasets obtained from different measurement apparatus. Such processing or display of image datasets obtained from different measurement apparatus requires registration of the image datasets to a common coordinate system with reference to a patient's anatomy, such that the same position can be attributed to the same anatomical feature in each dataset.

It is a feature of the embodiment of FIGS. 1 and 2, that the registration of image datasets obtained using different ones of the scanners 2, 4, 6 and stored at different servers 8, 10, 12 can be obtained without requiring the transmission of image datasets, or other large quantities of data, between the servers 8, 10, 12.

Figure 3:
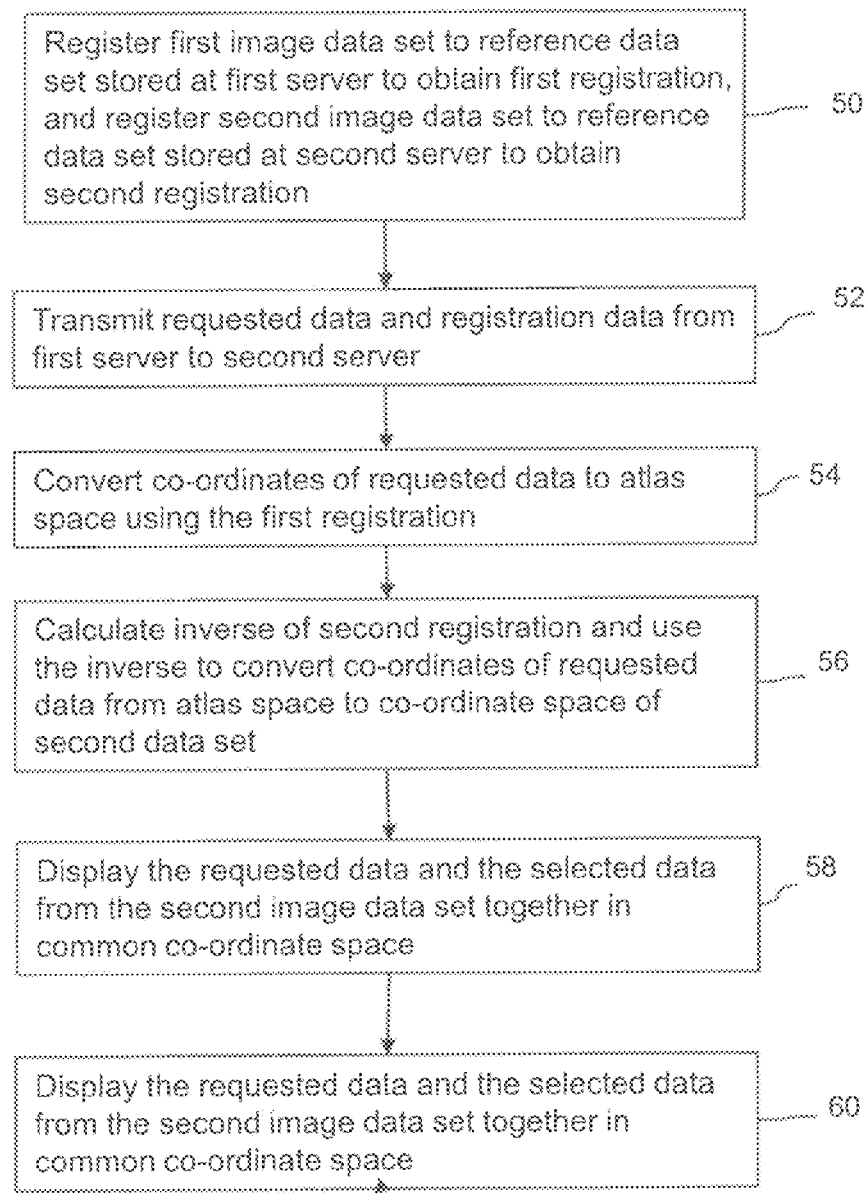
FIG. 3 is a flow chart illustrating a correlation process performed using the embodiment of FIG. 1.

FIG. 3 is a flowchart illustrating a registration and image processing performed by the embodiment of FIGS. 1 and 2. The processing procedure is able to obtain correlation of features in different CT and/or MR and/or PET image datasets or other image datasets without requiring pair wise comparisons or transmissions of bulk CT, MR or PET datasets between the servers 8, 10, 12.

As has already been mentioned above, in the embodiment of FIG. 1 a reference dataset in the form of a patient atlas dataset is stored at each of the servers 8, 10, 12. The patient atlas datasets are synthetic representations of generic patient anatomy in CT or MR. The atlas datasets are compiled during product development and embedded in each CT or MR server product during manufacture. Each atlas dataset may be of a similar data type to an actual CT or MR scan, or may be a richer or larger data type that also includes additional data, for example data comprising a vector of measurements or derived quantities at each spatial location, instead of the scalar measurements typically produced by CT or MR scanners.

The atlas is created by gathering enough actual CT or MR datasets such that the whole of the human body is represented, major anatomical variants due to sex and other differences are represented, and every part of the body is represented in a normal condition. As it is not practical or ethical to acquire scans of healthy subjects for the purpose of compiling the atlas, patient scans are used after appropriate anonymization and legal clearance. Many patient scans are in fact normal, in the sense that no pathology or deviation is visualised. Other datasets will show a combination of normal and abnormal anatomy. To use such scans, an expert annotates the normal and abnormal portions of the scan, so that only the normal portions are eligible for inclusion in the atlas. The expert may also indicate a classification by anatomical variant. Subsequently, the normal scan data is processed to classify it by anatomical variant and to merge the data from different scans in a way that facilitates registration. The resulting data is embedded in each CT, MR or PET scanner or associated server.

A single, combined atlas comprising all relevant atlas data can be used for registration with each patient image dataset in some embodiments. In other embodiments an atlas comprising a sub-set of atlas data can be selected based upon a characteristic of the patient. For instance, image data obtained for a female patient aged 63 could be registered to an atlas dataset comprising atlas data obtained only from female patients aged between 55 and 70.

In the embodiment of FIG. 1, the CT atlas datasets stored in the CT servers 8, 10 are identical and comprise CT data. The MR atlas dataset stored in the MR server 12 is different to the atlas dataset stored in the CT servers 8, 10, and comprises MR data rather than CT data. A prior registration process is performed that registers the CT atlas dataset and the MR atlas dataset. Registration data representing the registration, and enabling a mapping between positions in the MR atlas dataset and the CT atlas dataset, is stored in the servers 8, 10, 12 together with the respective atlas datasets. In alternative embodiments, an identical atlas dataset or other reference dataset is stored at each of the CT and MR servers 8, 10, 12.

As mentioned above, each image dataset is automatically registered to a reference after it has been obtained. In the case of the process of FIG. 3, at the first stage of the process 50 a first image dataset of a patient obtained using the CT scanner 2 is compared to the patient atlas dataset stored at the server 8 to yield a registration from the first image dataset to the patient atlas dataset. A known registration process is used for the comparison, for example comprising either or both rigid and non-rigid registration steps.

In one embodiment the registration comprises an initial matching procedure, in which an initial search is performed for an offset between the position of the patient atlas dataset and the position of the first dataset that provides an acceptable match between the image represented by the patient atlas dataset and the image represented by the first dataset. The initial matching procedure comprises performing a number of fast searches with different start positions in a transverse direction to determine a vertical offset between the reference dataset and the measurement dataset that is close to the true one. Any suitable search and matching procedure can be used, and may comprise any suitable optimisation technique or other technique for searching a solution space. In the embodiment of FIG. 1, Powell's method is used for the optimisation. Other optimisation methods that can be used include simulated annealing, the Broyden-Fletcher-Goldfarb-Shanno (BFGS) method, and the Simplex algorithm.

The offset or transformation obtained in the initial matching procedure is then used as a starting point, and in the next stage a further more precise matching procedure is performed that comprises searching for a rigid transformation that provides the best registration of the 3D image represented by the first image dataset with the 3D image represented by the patient atlas dataset. Again, any suitable optimisation technique or other technique for searching a solution space can be used. By using the offset or transformation obtained in the initial matching procedure as a starting point it can be ensured that the more precise matching procedure begins at a reasonable starting place, such that the search for the best rigid transformation does not get stuck at local maxima or minima of the search space.

In the embodiment of FIG. 1, the rigid transformation displaces and rotates the co-ordinates of the first image dataset as necessary, to obtain registration of the first image dataset to the patient atlas dataset. In alternative embodiments, a non-rigid transformation is used. In some such alternative embodiments, a rigid transformation is first obtained and used as the starting point for the search for the optimal non-rigid registration.

The data stored at the server and associated with the image dataset also includes, in this case, key image data representative of key images obtained from the first image dataset and selected by an operator, for example a radiologist, and notes or other information concerning findings of the operator.

Subsequently, an MR measurement is performed on the patient using the MR scanner 6 to produce a second image dataset of the patient. The second image dataset of the patient obtained using the MR scanner 6 is compared to the patient atlas dataset stored at the server 12 to yield a registration from the second image dataset to the patient atlas. Again, a known registration process is used for the comparison.

When an application running on one server needs to correlate anatomical features or images with anatomical features or images obtained from other scans of the patient stored at different servers, it converts the coordinates of the feature from the current scan space to atlas space. It then consults other servers or a repository to find a registration of a second scan to atlas space, computes the mathematical inverse of the registration, and uses the inverse registration to convert the coordinates of the first scan from atlas space to the space of the second scan.

For example, in the embodiment of FIG. 1, it may be desired to correlate both CT and MR measurements performed on the same patient, for example to correlate CT and MR image data. The operator, for example a radiologist, who used the MR scanner 6 to obtain the second image dataset, determines from computerised patient records associated with the patient, that a CT scan has already been performed. If the radiologist was administering both the CT and MR scans then he or she may be aware of the previous CT scans without consulting the records, and may perform the CT and MR scans as part of a combined CT and MR scanning program for the patient.

At stage 52 of the process of FIG. 3, the operator instructs the MR server 12 to transmit a message to CT server 8 requesting key image data representative of a key image obtained from the first image dataset. In response, the CT server 8 transmits to the MR server 12 the key image data, which is in accordance with a co-ordinate system of the first image dataset. The CT server 8 also transmits to the MR server 12 registration data representative of the registration of the first image dataset to the CT atlas dataset and, if necessary, data representative of the registration of CT atlas dataset to the MR atlas dataset.

The CPU 32 of the server 12 then, at stage 54 processes the registration data and converts the co-ordinates of the key image data received from the CT server 8 from a co-ordinate system of the first image dataset to CT atlas space, based upon the mapping of the first image dataset to the CT atlas dataset represented by the registration data.

In the embodiment of FIG. 1, the CT atlas dataset and the MR dataset are different, and so a further process is performed at stage 54, in which the co-ordinates of the key image data are converted from CT atlas space to MR atlas space.

At stage 56, the CPU 32 of the server 12 then computes the inverse of the mapping of the second image dataset to the MR atlas dataset, and then uses the inverse to convert the key image data obtained from the first image dataset (the CT image dataset in this case) to the co-ordinate space of the second image dataset (the MR image dataset).

At stage 58 the CPU 32 of the server 12 selects data from the second image dataset (the MR image dataset in this case) corresponding to the co-ordinates of the key image data of the first image dataset (the CT image dataset in this case).

At stage 60 the server 12 processes the CT key image data and the corresponding MR image data, and renders and displays them simultaneously or successively in a common co-ordinate space, in this case the co-ordinate space of the second image dataset. The images will appear congruent if displayed side by side.

By comparing each CT or MR dataset with a locally-stored reference, and then correlating different CT or MR datasets based upon the mapping to a common reference space, registrations between any two datasets stored at different locations can be computed without requiring the transmission of the datasets between the locations. Correlation of features in different CT and MR datasets can be achieved without any pair-wise comparisons or transmissions of CT or MR data between servers. The process is based upon the fact that given registrations A→B, B→C and A→C, the mathematical combination of (A→, B→C) is an approximation of A→C. The process enables a great reduction in the volume of data that needs to be transmitted between servers to enable correlation between different scans, whilst also allowing for a distributed server architecture to be used.

The process uses O(N) comparisons to register each of N scans with the atlas, and does not require any communication of CT or MR data to achieve the registration, unless so desired. Usually only a small amount of registration data is communicated between different servers in order to achieve the registration.

The processing and display of the data can be performed at any one of the servers or other devices in alternative embodiments. For example, key images from the CT and MR data sets can be transmitted to the client server 18, and displayed on the display 20 in a common co-ordinate space. The display of images or other data from the first image dataset and the second image dataset can be in any common co-ordinate space, for example in atlas space, in a co-ordinate space of the first image dataset or in a co-ordinate space of the second image dataset.

In the process described in relation to FIG. 3, the correlation between the CT and MR image datasets is used to select and display key image data from the CT dataset and corresponding MR image data from the MR image dataset. However, the process is not limited to displaying key image data and can be used to correlate any suitable process between different image datasets. For example, the processing may comprise performing image analysis functions such as measurements or identification of structures, as well as rendering functions such as presenting cross sections, projections, surface renderings, and other synthetic images generated from the acquired data. The correlation, based on registration to the common atlas space, ensures that such processes are performed on corresponding parts of different image datasets, without requiring a direct registration between the image datasets.

In a further embodiment, the system is used to track changes in image data representative of changes in patient anatomy, over time. The image data can be obtained using the same or different measurement apparatus, for example the same or different CT scanner.

For example the system can be used to track lung nodules over time. Each time the patient has a CT scan, the application running on the CT server 8 has access to the current CT dataset and can locate and measure the lung nodules present in that current dataset. The location of each nodule is converted to patient atlas coordinates based on the registration of the dataset to the locally stored patient atlas dataset. Subsequently the location of each nodule can be correlated with locations of nodules in previously obtained datasets obtained from CT or other measurement on the patient, based on the mapping to the mutual atlas space. Thereby, the progress of disease can be charted, without requiring direct registration between datasets obtained at different times. The time-consuming manual step of matching nodules of the current measurement dataset with nodules obtained from previous measurement datasets can be avoided.

Figure 4:
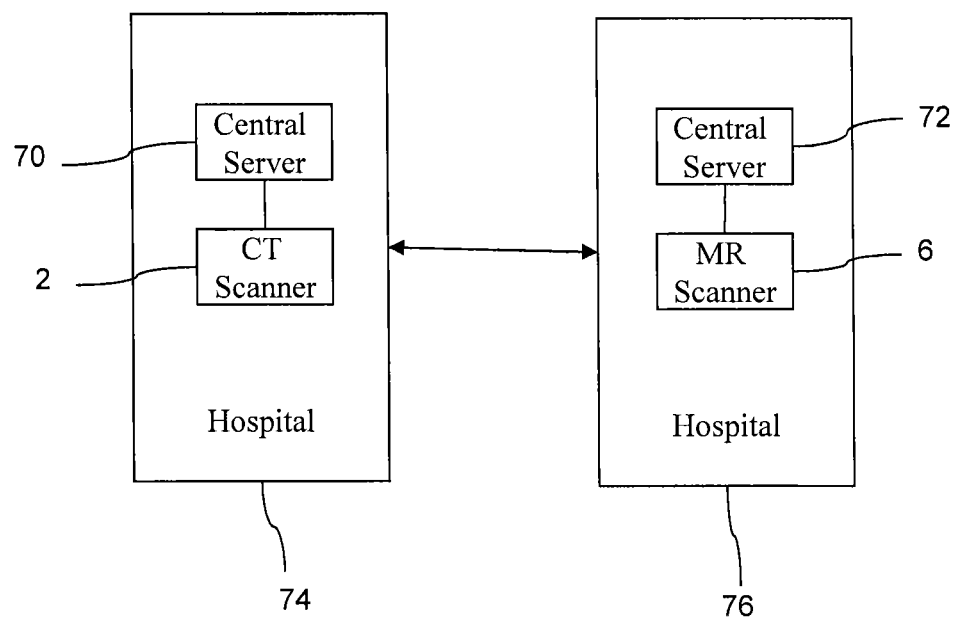
FIG. 4 is a schematic diagram of an image data processing system according to a further embodiment.
Figure 5:
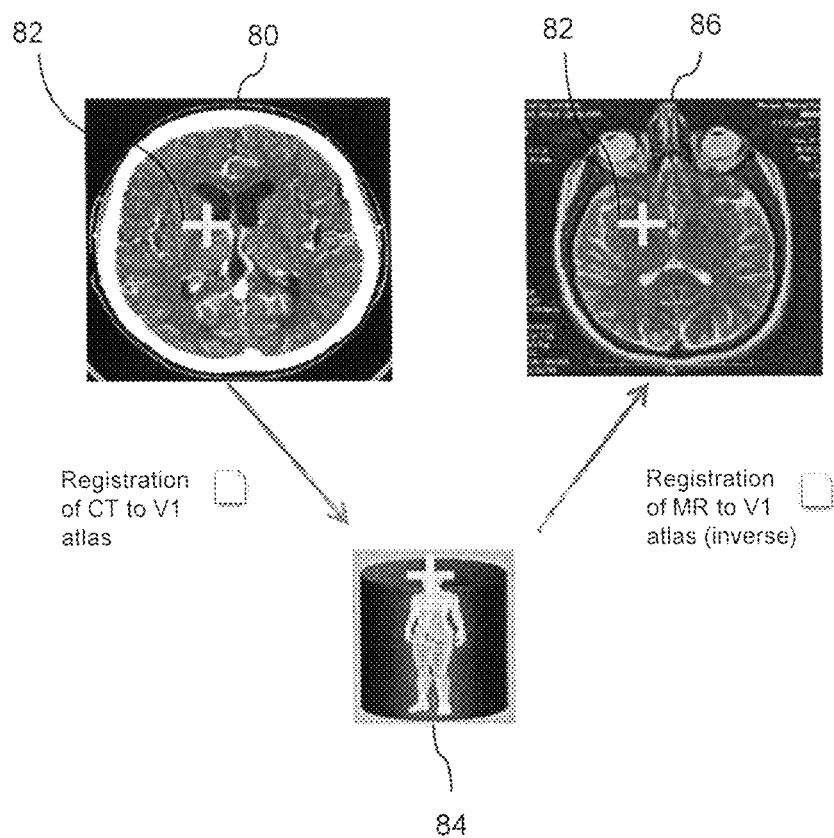
FIG. 5 is a diagram showing the results of a correlation process.

Another embodiment in which the system is used to track changes over time is illustrated with reference to FIGS. 4 and 5. FIG. 4 shows a further embodiment of a medical imaging system in which the CT scanner 2 and the MR scanner 6 are at different locations for example in different hospitals. In this case, the system does not have a distributed server architecture. Instead data from the CT scanner 2 is provided to and stored at a central server 70 forming part of a PACS system at hospital 74. The data from the MR scanner 4 is provided to and stored at a central server 72 forming part of a PACS system at hospital 76.

A CT measurement is performed on a patient by the CT scanner 2, and the CT measurement data is mapped to an atlas dataset stored at the CT scanner 2. The CT measurement data and registration data representative of the mapping is subsequently stored at the server 70. Analysis is also performed on the CT measurement dataset by an operator and data representative of the findings of the operator are also stored with the CT measurement dataset at the server 70. In this case, the operator discovers a lesion in a brain slice, and the location of the lesion together with a key image representative of the brain slice is stored with the CT measurement dataset. The key image 80 and the location 82 of the lesion are shown in FIG. 5.

Subsequently, an MR scan is performed on the same patient using the MR scanner 6 at hospital 76. A mapping of the MR scan data to an atlas dataset 84 stored at the MR scanner 6 is performed automatically once the MR scan data has been obtained. The atlas dataset is the same as that stored at the CT scanner 2. The MR scan dataset and mapping data representative of the mapping to the atlas dataset is subsequently stored at the server 74.

A radiologist at hospital 76 reviews the MR dataset and notes from computerised patient records for the patient that a CT scan has previously been performed. The radiologist sends a request for information concerning the previous CT scan to the server 70 at hospital 74. The server 70 returns the key image data obtained from the CT scan together with location data representative of the lesion and mapping data representative of the mapping to the atlas dataset.

Application software running at the server 74, or on a user terminal (not shown) linked to the server 74 determines the location of the lesion from the data sent from the server 70, and converts that location to a location in atlas space using the mapping data (representative of the mapping of the CT dataset to the atlas) obtained from server 70 The application software determines, using the inverse of the registration of the MR dataset to the atlas dataset, an equivalent location in MR dataset space and selects a portion of the MR dataset representative of that equivalent location. The application software processes the selected portion of the MR dataset to generate an image that is geometrically congruent with the CT key image received from the server 70.

In the embodiment of FIGS. 1 and 4, findings obtained from a prior CT scan obtained at one hospital or other location can be overlaid on data obtained from a subsequent MR scan obtained at another hospital or another location in a common coordinate system, without requiring the transmission of the bulk CT or MR scan data.

In a variant of the embodiment of FIG. 4, the location of the lesion is converted to atlas space at the server 70, rather than at the server 74, and the co-ordinates of the lesion in atlas space are transmitted from the server 70 to the server 74.

In the embodiment of FIGS. 1 and 4, the imaging datasets at different locations are mapped to a patient atlas. However, the system is not limited to mapping to a patient atlas and the mapping can be performed to any suitable reference. In certain embodiments, each of the datasets obtained from the same patient at a different location or different time is mapped to a list of anatomical landmarks. In such embodiments, any suitable known automatic or manual process for identifying the location of the anatomical landmarks in the image dataset can be used.

Examples of anatomical features that can be used as anatomical landmarks include the centre of gravity of the C5 left vertebra (or other vertebra), the centre of the left femur head, the left and right coronary ostia, the bifurcation point of the left internal iliac artery, the midpoint of the anterior communicating artery of the circle of Willis, the anterior and posterior commissures in the brain, the tip of the pancreatic head, the bifurcation of the bile duct, the centre of gravity or other geometric measures of the left kidney, the distal attachment point of the left bicep to the radius, and numerous other features based on skeletal, neural, vascular, or other organ morphology.

The main requirements for a feature to be used as an anatomical landmark is that it be precisely and unambiguously defined and that there exists at least one algorithm that automatically locates the feature in CT, MR, or PET scans or a combination of such scans with a useful probability of yielding correct results. Any suitable number of anatomical features may be used, for example twenty or more in some embodiments. It is not essential that every feature be identified in every dataset, or even that each identified feature is located correctly, so long as a sufficient subset of features are identified and is located correctly in both datasets.

In one embodiment, CT scans of the same patient are obtained at different times and in different locations, for example using a CT scanner in a hospital and subsequently using a CT scanner in a CT scanner truck. The first set of CT data, obtained using the CT scanner in the hospital is processed to identify the location of each of the anatomical landmarks, and first mapping data representative of the anatomical landmarks locations is stored with the first set of CT data. In principle landmarks could be identified by the operator but this becomes impractical beyond a very small number of landmarks. In the present embodiment, as many landmarks as possible are identified by automatic processing. In this case, an operator also identifies from the first set of CT data the position of a nodule, and the nodule position is also stored with the first set of CT data.

Subsequently, the second set of CT data, obtained using the CT scanner in the CT scanner truck, is also processed, using application software at an operator terminal, to identify the location of each of the anatomical landmarks and data representative of the locations of the anatomical landmarks is stored with the second set of CT data.

The operator determines from computerised patient records for the patient that a CT scan has previously been performed by the hospital, and sends a request to a server at the hospital for data relating to the CT scan. In response, the server at the hospital transmits to the operator terminal at the CT scanner truck the first mapping data representative of the identified locations of the anatomical landmarks in the first set of CT data. The server at the hospital also transmits the data representative of the nodule position determined from the first set of CT data, and other related information, for example notes made by the operator at the hospital.

The application software running at the operator terminal at the CT scanner truck then performs a mapping process to map the point locations in three dimensions of the anatomical landmarks determined from the first CT dataset to the locations of the corresponding anatomical landmarks determined from the second CT dataset. Any suitable known process for matching the locations of two sets of identified points in three directions can be used, so long as it is robust to the presence of wrongly identified or inaccurately located points. For example this can be achieved by selecting the common subset of points that has been identified in both the first and the second dataset and then performing a least-squares regression of an affine transformation.

The mapping is then used to map the nodule position determined from the first CT dataset to a corresponding position in the second CT dataset. The application software can then render and display the second CT image dataset on a display device at the CT scanner truck, including a display indicator showing the position of the nodule previously determined from the first CT dataset, thus enabling an operator to determine whether any new nodules have developed. Thus, results obtained from a previous scan can be registered to and displayed with the results of a later scan performed at a different location, without requiring the transmission of full image datasets in order to perform the registration.

In the embodiment of FIG. 1, the patient atlas stored at each of the CT scanners 2, 4 is the same, and is registered to the corresponding patient atlas or other reference stored at the MR scanner 6. Over time, the library of normal data and registration technology available to construct the atlas or other reference may improve. This makes possible the construction of a new patient atlas or other reference which allows more accurate registration for a greater percentage of patients. In further embodiments, both the old (version 1) and new (version 2) atlases are embedded in every scanner manufactured after the new atlas is available. Each scanner performs registration of datasets to each of the atlases (for example version 1 and version 2 atlases) or other references that are stored at the scanner, and each registration result is stored with the datasets.

Figure 6:
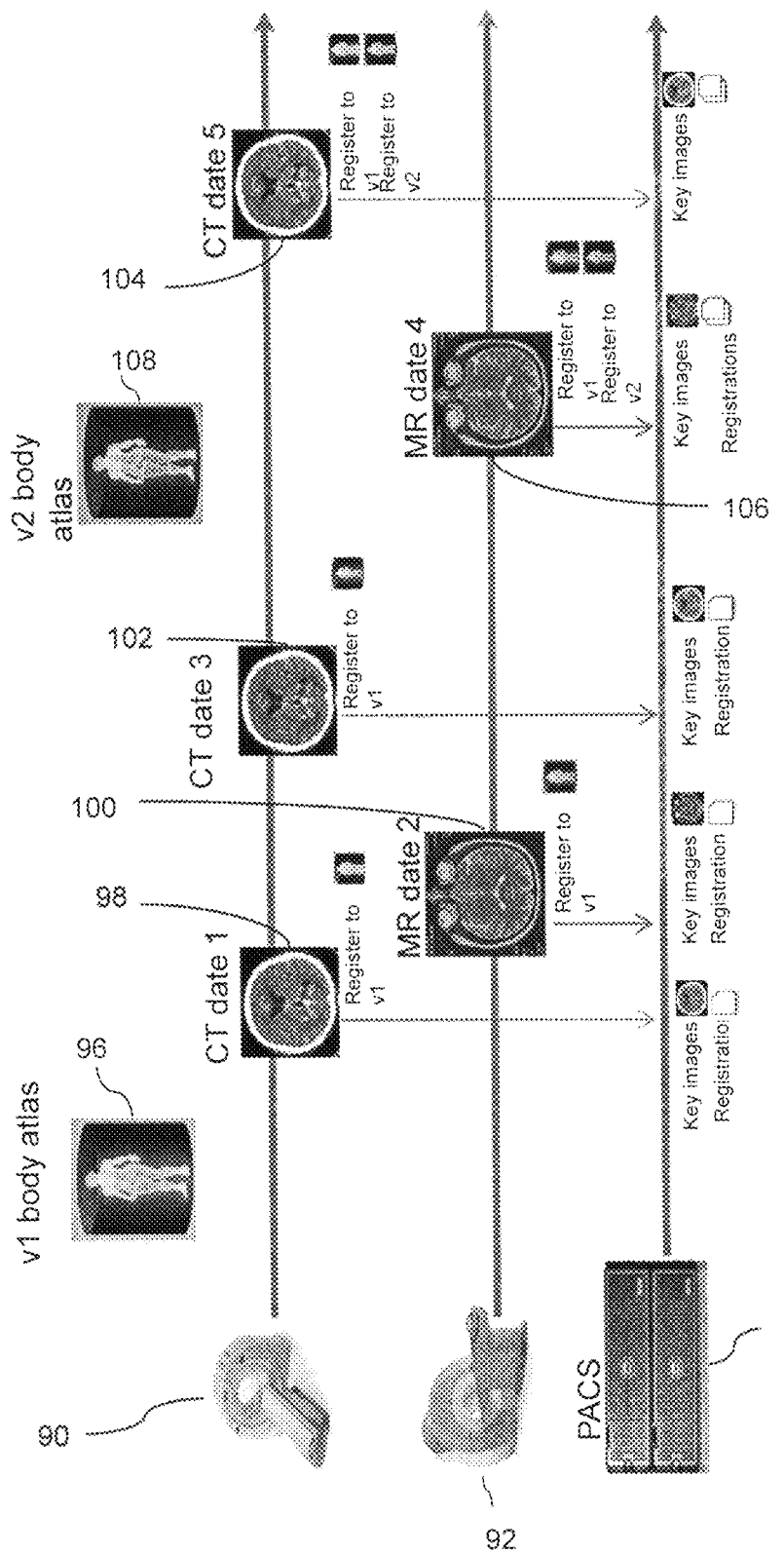
FIG. 6 is a schematic diagram showing a timeline of image datasets obtained using different scanners.

Subsequently, comparisons between scans are possible using the best registration that is available for both scans. For example, if a previous scan has only been registered to the version 1 atlas and a current scan is registered to both the version 1 atlas and the version 2 atlas, only the version 1 atlas registration would be used to correlate the previous and current scans. In contrast, if a further scan was registered to both the version 1 atlas and the version 2 atlas, the version 2 atlas registration would be used to correlate the current scan and the further scan. Operation of one such embodiment is illustrated schematically in FIG. 6, which shows a timeline of various actions performed using a CT scanner 90, an MR scanner 92 and a PACS server 94, connected to the CT scanner 90 and MR scanner 92 via a network.

At the beginning of the timeline a first version of a patient atlas 96, referred to as the V1 atlas, is stored at both the CT scanner 90 and the MR scanner 92. At a first time, referred to as CT date 1, a first CT image dataset 98 is obtained from measurements on a patient using the CT scanner. The CT image dataset 98 is registered to the V1 atlas. Registration data representative of the registration to the V1 Atlas is transmitted to and stored at the PACS server 94. The CT image dataset 98 is stored at the CT scanner 90.

Subsequently, MR measurements are performed on the patient using MR scanner 92, at MR date 2, to obtain a first MR image dataset 100. The MR image dataset 100 is registered to the V1 atlas, and registration data representative of the registration to the V1 atlas is transmitted to and stored at the PACS server 94. The MR image dataset 100 is stored at the MR scanner 92.

Further CT measurements 102, 104 are performed on the patient using CT scanner 90 at CT date 3 and at CT date 5. A further MR measurement 106 is performed on the patient using MR scanner 92 at MR date 4. As with the earlier CT and MR measurements, a registration to the V1 atlas is performed and key images and registration data are transmitted to and stored at the PACS server 94.

An updated patient atlas, referred to as the V2 atlas 108, was distributed to and stored at the CT scanner 90 between CT date 3 and MR date 4. Thus, the MR measurement 106 performed at MR date 4 and the CT measurement 104 performed at CT date 5 is also registered to the V2 atlas 108, and registration data representative of that mapping to the V2 atlas 108 is also transmitted to and stored at the PACS server 94.

Subsequently if, for example, MR image dataset 106 is to be correlated to CT image dataset 98, then the registrations to the V1 atlas will be used to determine the correlation. In contrast, if MR image dataset 106 is to be correlated to CT image dataset 104 then the registrations to the V2 atlas will be used to determine the correlation as both MR image dataset 106 and CT image dataset 104 have been registered to the V2 atlas.

In the described embodiments the same reference, for example the same atlas dataset, has been used for registration of an image dataset regardless of the particular part of the image dataset, for example the particular anatomical feature, that is of interest. In alternative embodiments, a part of the reference, for example a part of the atlas dataset, is selected for use in the registration and mapping in dependence on the particular part of the image dataset, for example a particular anatomical feature, that is of interest.

For example, if an operator is interested in the cardiac system of a patient, then an atlas selection step may be performed prior to registration, in which a part of the patient atlas dataset representative of the chest region is selected, and only that part of the patient atlas dataset is used in subsequent registration and mapping of the image dataset. Thus, a more accurate registration of the chest region may be obtained than if the whole atlas dataset is used for the registration and mapping. A similar procedure can be used in such alternative embodiments in cases where the reference comprises a list of anatomical features. In such cases for such alternative embodiments, only those anatomical features located within or close to the chest region may be selected to be used in the registration and mapping.

Although the described embodiments have related to the correlation of CT, MR and PET image datasets, it will be understood that in alternative embodiments the methods and systems described herein can be used to correlate any suitable image datasets.

While certain embodiments have been described, these embodiments have been presented by way of example only, and are not intended to limit the scope of the inventions. Indeed the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms and modifications as would fall within the scope of the invention.

The invention claimed is:

1. A method of processing medical image data comprising:
   performing at a first location a first mapping process to obtain a mapping between a first medical image dataset having a first co-ordinate system and a first reference dataset representative of human anatomy and having a reference co-ordinate system;
   performing at a second location a second mapping process to obtain a mapping between a second medical image dataset having a second different co-ordinate system and a second reference dataset representative of human anatomy and having the reference co-ordinate system, wherein the second location is remote from the first location;
   transmitting at least one message from the first location, the at least one message including mapping data representative of the mapping between the first medical image dataset and the first reference dataset representative of human anatomy; and
   receiving the message and using the mapping data of the received message and the second mapping to correlate at least one position in the first co-ordinate system to at least one position in the second co-ordinate system, wherein the at least one message including mapping data transmitted from the first location does not include at least the whole of the first medical image dataset.

2. The method according to claim 1, wherein the first reference dataset comprises a first atlas dataset and the second reference dataset comprises a second atlas dataset.

3. The method according to claim 1, wherein the first reference dataset and the second reference dataset each comprises a list of anatomical features.

4. The method according to claim 1, wherein the first reference dataset is identical to the second reference dataset.

5. The method according to claim 1, wherein the first reference dataset is different to the second reference dataset.

6. The method according to claim 1, wherein the first reference dataset is stored at the first location and the second reference dataset is stored at the second location remote from the first location.

7. The method according to claim 6, wherein the first reference dataset is stored at a first image processing sub-system and the second reference dataset is stored at a second image processing sub-system remote from the first image processing sub-system.

8. The method according to claim 7, wherein the first image processing sub-system comprises a first computed tomography (CT), magnetic resonance (MR), or positron emission tomography (PET) scanner, and the second image processing sub-system comprises a second CT, MR, or PET scanner.

9. The method according to claim 8, wherein each image processing sub-system is operable to obtain a plurality of sets of image data, and each image processing sub-system is configured to map each set of image data obtained to the first reference dataset or the second reference dataset, and to store mapping data representative of the mapping.

10. The method according to claim 1, further comprising processing the mapping data and the second mapping at the second location to correlate the at least one position in the first co-ordinate system to the at least one position in the second co-ordinate system.

11. The method according to claim 1, wherein the at least one message comprises image data or anatomical feature data obtained from or representative of at least one position in the first co-ordinate system, and the method further determining a corresponding at least one position in the second co-ordinate system of the second image dataset or a corresponding at least one position in the reference co-ordinate system.

12. The method according to claim 11, further comprising displaying the image data or anatomical feature data in the second co-ordinate system or in the reference co-ordinate system.

13. The method according to claim 1, further comprising performing a first image processing procedure on the first image dataset and performing a second image processing procedure on the second image dataset, and using the correlation of the at least one position in the first co-ordinate system to the corresponding at least one position in the second co-ordinate system to correlate the first and second image processing procedures.

14. The method according to claim 13, further comprising performing the first image processing procedure on data of the first image dataset representative of a selected anatomical feature or region, and the correlating of the first and second image processing procedures further comprises performing the second image processing procedure on data of the second image dataset representative of a corresponding anatomical feature or region.

15. The method according to claim 14, further comprising displaying on a display an image of the selected anatomical feature or region and an image of the corresponding anatomical feature or region, simultaneously or successively in a sequence.

16. The method according to claim 13, wherein at least one of the first image processing procedure and the second image processing procedure comprises one or more of:
   selecting image data;
   rendering image data for display;
   performing a measurement;
   identifying a structure; and
   transmitting image data to a central server.

17. An imaging apparatus configured to obtain a first image dataset having a first co-ordinate system, the apparatus comprising:
   a memory storing a first reference dataset representative of human anatomy and having a reference co-ordinate system; and
   a processing resource configured to map the first image dataset to the first reference dataset, wherein
   the processing resource is further configured to receive from a remote location mapping data representative of a mapping of a second image dataset having a second different co-ordinate system to a further reference dataset representative of human anatomy and having the reference co-ordinate system, and to use the received mapping data and the mapping of the first image dataset to the first reference dataset to correlate at least one position in the first co-ordinate system and at least one position in the second co-ordinate system.

18. The apparatus according to claim 17, further comprising an imaging apparatus for obtaining the first image dataset.

19. The apparatus according to claim 18, further comprising a data obtaining part configured to obtain a plurality of sets of image data, and wherein the processing resource is configured to map each of the plurality of sets of image data to the first reference dataset and, for each mapping, to store mapping data representative of the mapping.

20. An image processing system comprising:
   a first image processing sub-system at a first location, storing a first reference dataset representative of human anatomy;
   a second image processing sub-system at a second location, storing a second reference dataset representative of human anatomy; and
   a processing resource, wherein
   the first image processing sub-system is configured to perform a first mapping process to obtain a first mapping between a first medical image dataset having a first co-ordinate system and the first reference dataset,
   the second image processing sub-system is configured to perform a second mapping process to obtain a second mapping between a second image dataset having a second co-ordinate system and the second reference dataset,
   the first image processing sub-system is configured to transmit to the processing resource at least one message including mapping data representative of the mapping between the first medical image dataset and the first reference dataset,
   the processing resource is configured to receive the at least one message and to use the mapping data from the at least one message and the second mapping to correlate at least one position in the first co-ordinate system and at least one position in the second co-ordinate system, and
   the at least one message including mapping data transmitted from the first location does not include at least the whole of the first image dataset.

21. The system according to claim 20, wherein the processing resource is provided in the second image processing sub-system.

* * * * *